(12) United States Patent
Horn

(10) Patent No.: US 11,717,478 B2
(45) Date of Patent: *Aug. 8, 2023

(54) METHODS FOR IMPROVING VISION

(71) Applicant: Eye Therapies, LLC, Dana Point, CA (US)

(72) Inventor: Gerald Horn, Deerfield, IL (US)

(73) Assignee: EYE THERAPIES LLC, Dana Point, CA (US)

( * ) Notice: Subject to any disclaimer, the term of this patent is extended or adjusted under 35 U.S.C. 154(b) by 195 days.

This patent is subject to a terminal disclaimer.

(21) Appl. No.: 17/318,562

(22) Filed: May 12, 2021

(65) Prior Publication Data

US 2021/0259962 A1    Aug. 26, 2021

Related U.S. Application Data

(63) Continuation of application No. 16/253,349, filed on Jan. 22, 2019, now Pat. No. 11,026,884.

(60) Provisional application No. 62/621,080, filed on Jan. 24, 2018.

(51) Int. Cl.

| | | |
|---|---|---|
| *A61K 31/4965* | (2006.01) | |
| *A61P 27/06* | (2006.01) | |
| *A61K 9/00* | (2006.01) | |
| *A61K 31/498* | (2006.01) | |
| *A61K 47/26* | (2006.01) | |
| *A61K 47/38* | (2006.01) | |
| *A61K 47/10* | (2017.01) | |
| *A61K 47/12* | (2006.01) | |
| *A61K 47/34* | (2017.01) | |
| *A61K 47/40* | (2006.01) | |
| *A61K 47/44* | (2017.01) | |
| *A61K 47/18* | (2017.01) | |
| *A61K 47/02* | (2006.01) | |

(52) U.S. Cl.
CPC .......... *A61K 9/0048* (2013.01); *A61K 31/498* (2013.01); *A61K 47/02* (2013.01); *A61K 47/10* (2013.01); *A61K 47/12* (2013.01); *A61K 47/186* (2013.01); *A61K 47/26* (2013.01); *A61K 47/34* (2013.01); *A61K 47/38* (2013.01); *A61K 47/40* (2013.01); *A61K 47/44* (2013.01); *A61P 27/06* (2018.01)

(58) Field of Classification Search
CPC .............................. A61K 31/4965; A61P 27/06
USPC ...................................................... 514/255.05
See application file for complete search history.

(56) References Cited

U.S. PATENT DOCUMENTS 11,026,884 B2 *   6/2021   Horn ....................... A61P 27/06

* cited by examiner

*Primary Examiner* — Raymond J Henley, III

(74) *Attorney, Agent, or Firm* — Wood, Phillips, Katz, Clark & Mortimer

(57) ABSTRACT

The present invention is directed to methods for improving night vision and visual performance in low light conditions comprising ophthalmological administration of compositions comprising low dose brimonidine and a vehicle for improved performance.

17 Claims, No Drawings

METHODS FOR IMPROVING VISION

FIELD OF THE INVENTION

The present invention relates to methods for improving night vision and visual performance in low light conditions comprising ophthalmological administration of compositions comprising low dose brimonidine and a vehicle for improved performance.

BACKGROUND OF THE INVENTION

Glare and halo have long been known to be associated with optical imperfections of the cornea, particularly spherical aberrations. Night vision is particularly sensitive to such aberrations, where a peripheral ring of cornea does not have the same focal point as the sharper acuity central corneal zones, resulting in haloing. Other aberrations include coma and together these aberrations additionally cause streaking of light, and glare. Studies on subjects under conditions of increased pupil size such as cloudy days or suboptimal indoor lighting increased aberrations and can cause a large reduction in contrast acuity. Increase in pupil area of as little as 10 $mm^2$ has been associated with reduced visual performance, increased fatigue, and may also adversely affect sports performance. Taken to an extreme, such as under conditions of pharmacologic dilation, even daytime driving performance deteriorates, including but not limited to gap perception and road sign distance deterioration. Boyce, P R et al., The impact of spectral power distribution on the performance of an achromatic visual task, *Lighting Research and Technology*, Jun. 1, 2003; Pupil dilatation does affect some aspects of daytime driving performance. *Br J Ophthalmol*, 2003 November: 87(11): 1387-90.

Corneal and cataract surgery may induce spherical aberrations similarly reducing vision and vision performance, particularly in reduced lighting conditions such as night driving. Radial keratotomy, automated lamellar keratoplasty, and more recently laser vision correction have been demonstrated to, in some cases, induce spherical aberration and other higher order optical aberrations, as may cataract surgery. As little as 0.5 mm reduction in pupil size significantly reduces spherical aberration in almost all cases, as these aberrations are most severe near the margins of the scotopic pupil, as they are inversely proportional to optical zone size.

A further issue is reduced vision in low light conditions. For example, under conditions where luminance is below 500 candela per square meter visual acuity is reduced. These low light conditions may occur indoors or outdoors and can affect performance in a variety of tasks such as work and sports.

It is possible to pharmacologically modify the pupil and improve vision. This improvement can be measured either indirectly as a reduction in Snellen acuity (high contrast) or more commonly reduction in low contrast acuity (mesopic or scotopic). This improvement can also be measured more directly as a reduction in aberrations via wave front aberrometry, which allows quantifying the aberrations themselves. Historically, miotics have been used to reduce pupil size, and thereby filter out peripheral corneal, corneal inlay, lenticular, or lens implant induced (post cataract surgery) aberrations. Dilute miotics, such as pilocarpine and aceclidine, along with brimonidine typically 0.15% to 0.20% have been used to effect pupil size reduction and documented improvement in night vision. Miotics are difficult to use for this purpose, causing ciliary pain, tachyphylaxis, some induced myopia depending on concentration used, and may cause undesirable dimming from excessive peak constriction.

Thus, there is a need in the art for a method of improving vision without the attendant side effects.

SUMMARY OF THE INVENTION

In one embodiment, the present invention is directed to a method of improving night vision comprising administering to an eye of subject in need thereof a composition comprising from about 0.01% to about 0.05% w/v brimonidine, from about 1% to about 5% w/v of a nonionic surfactant and a viscosity enhancer, wherein the composition has a pH from about 6.0 to about 8.0.

In one embodiment, the present invention is directed to a method of improving sports performance under a luminance level below 500 candela per square meter ("$cd/m^2$") comprising administering to an eye of subject in need thereof a composition comprising from about 0.01% to about 0.050% w/v brimonidine, from about 1% to about 5% w/v of a nonionic surfactant and a viscosity enhancer, wherein the composition has a pH from about 6.0 to about 8.0.

In one embodiment, the present invention is directed to a method of improving eye fatigue under a luminance level below 500 $cd/m^2$ comprising administering to an eye of subject in need thereof a composition comprising from about 0.01% to about 0.050% w/v brimonidine, from about 1% to about 5% w/v of a nonionic surfactant and a viscosity enhancer, wherein the composition has a pH from about 6.0 to about 8.0.

DETAILED DESCRIPTION OF THE INVENTION

In one embodiment, the present invention is directed to a method of improving night vision comprising administering to an eye of subject in need thereof a composition comprising from about 0.01% to about 0.05% w/v brimonidine, preferably from about 0.015% to about 0.040% w/v, from about 1% to about 5% w/v of nonionic surfactant, preferably selected from the group consisting of a polysorbate, a poloxamer, a polyoxyl, an alkyl aryl poly ether, a cyclodextrin and a tocopheryl polyethylene glycol succinate, more preferably a polysorbate, even more preferably polysorbate 80 and a viscosity enhancer, preferably selected from hydroxypropylmethyl cellulose and carboxymethyl cellulose, preferably at a concentration from about 0.1% to about 2% w/v, more preferably from about 1.0% to about 1.25% w/v, optionally, from about 0.1% to about 5% w/v mannitol, optionally, from about 1 to about 10 millimolar boric acid and optionally, from about 0.05% to about 0.5% w/v sorbate, wherein the composition has a pH from about 6.0 to about 8.0.

In one embodiment, the present invention is directed to a method of improving sports performance or reduce eye fatigue under a luminance level below 500 $cd/m^2$), preferably below 10 $cd/m^2$ and more preferably below $1\times10^{-3}$ $cd/m^2$, comprising administering to an eye of subject in need thereof a composition comprising from about 0.01% to about 0.05% w/v brimonidine, preferably from about 0.015% to about 0.040% w/v, from about 1% to about 5% w/v of nonionic surfactant, preferably selected from the group consisting of a polysorbate, a poloxamer, a polyoxyl, an alkyl aryl poly ether, a cyclodextrin and a tocopheryl polyethylene glycol succinate, more preferably a polysorbate, even more preferably polysorbate 80 and a viscosity enhancer, preferably selected from hydroxypropylmethyl cellulose and carboxymethyl cellulose, preferably at a concentration from about 0.1% to about 2% w/v, more preferably from about 1.0% to about 1.25% w/v, optionally, from about 0.1% to about 5% w/v mannitol, optionally, from about 1 to about 10 millimolar boric acid and optionally, from about 0.05% to about 0.5% w/v sorbate, wherein the composition has a pH from about 6.0 to about 8.0.

In one embodiment, the present invention is directed to a method of improving eye fatigue under a luminance level below 500 cd/m$^2$, preferably below 100 cd/m$^2$ and more preferably below 10 cd/m2 and even more preferably below $1 \times 10^{-3}$ cd/m$^2$ comprising administering to an eye of subject in need thereof a composition comprising from about 0.01% to about 0.050% w/v brimonidine, preferably from about 0.015% to about 0.040% w/v, from about 1% to about 5% w/v of nonionic surfactant, preferably selected from the group consisting of a polysorbate, a poloxamer, a polyoxyl, an alkyl aryl poly ether, a cyclodextrin, a tocopheryl polyethylene glycol succinate, a glucosyl dialkyl ethers and a crown ether, ester-linked surfactants, more preferably a polysorbate, even more preferably polysorbate 80 and a viscosity enhancer, preferably selected from hydroxypropylmethyl cellulose and carboxymethyl cellulose, preferably at a concentration from about 0.1% to about 2% w/v, more preferably from about 1.0% to about 1.25% w/v, optionally, from about 0.1% to about 5% w/v mannitol, optionally, from about 1 to about 10 millimolar boric acid and optionally, from about 0.05% to about 0.5% w/v sorbate, wherein the composition has a pH from about 6.0 to about 8.0.

In a more preferred embodiment, administration of compositions of the present invention occurs once or twice daily.

In another more preferred embodiment, administration of compositions of the present invention once or twice daily provides improvement of night vision that occurs for at least four weeks without tachyphylaxis.

In another more preferred embodiment, administration of compositions of the present invention provides a reduction in the diameter of the pupil of the eye of the subject by 0.5 millimeters or more for 6 or more hours.

Compositions of the present invention have a pH from about 6.0 to about 8.0, preferably from about 6.5 to about 7.5 and most preferably about 7.5

The term "brimonidine" encompasses, without limitation, brimonidine salts and other derivatives, and specifically includes, but is not limited to, brimonidine tartrate, 5-bromo-6-(2-imidazolin-2-ylamino)quinoxaline D-tartrate, Alphagan (Alphagan is a registered trademark of Allergan, Inc.), and UK14,304.

Brimonidine may be present in compositions of the present invention at a concentration from about 0.01% to about 0.050% w/v, from about 0.02% to about 0.045% w/v or from about 0.015% to about 0.040% w/v.

Polysorbates suitable for use in the present invention include, but are not limited to, polysorbate 20 (polyoxyethylene (20) sorbitan monolaurate), polysorbate 40 (polyoxyethylene (20) sorbitan monopalmitate), polysorbate 60 (polyoxyethylene (20) sorbitan monostearate) and polysorbate 80 (polyoxyethylene (20) sorbitan monooleate).

Cyclodextrins suitable for use in the present invention include, but are not limited to, ionically charged (e.g. anionic) beta-cyclodextrins with or without a butyrated salt (Captisol) 2-hydroxypropyl beta cyclodextrin ("HPβCD"), alpha cyclodextrins and gamma cyclodextrins.

Poloxamers include but are not limited to poloxamer 103, poloxamer 123, and poloxamer 124, poloxamer 407, poloxamer 188, poloxamer 338 and any poloxamer analogue or derivative.

Polyoxyls include but are not limited to Brij® 35, 78, 98, 700 (polyoxyethylene glycol alkyl ethers) and Spans (sorbitan esters) and Span® 20-80 (sorbitan monolaurate, sorbitan monopalmitate, sorbitan monostearate, and sorbitan monooleate).

As used herein, all numerical values relating to amounts, weights, and the like, that are defined as "about" each particular value is plus or minus 10%. For example, the phrase "about 5% w/v" is to be understood as "4.5% to 5.5% w/v." Therefore, amounts within 10% of the claimed value are encompassed by the scope of the claims.

As used herein "% w/v" refers to the percent weight of the total composition.

As used herein, the term "administration" or "administering" refers to topical application, injection or administration via implants.

The articles "a," "an" and "the" are intended to include the plural as well as the singular, unless the context clearly indicates otherwise.

EXAMPLE 1 (VIRTUAL)

Methods

Ten subjects were administered one to two drops daily of each composition of Table 1, below for a four-week period. If a subject was administered more than one composition, then that subject has a one-week washout period following the last administration of the prior composition. Each of the ten subjects were required to (1) experience glare halo, 2) have high spherical aberration as detected by a wavefront aberrometer and 3) have a positive light flash test. A positive light flash test consists of improvement in contralateral eye when a pen light is used to illuminate the opposite eye.

TABLE 1

Miosis following instillation of brimonidine compositions

| Composition | 1 | 2 | 3 | 4 | 5 |
|---|---|---|---|---|---|
| Brimonidine | 0.015% | 0.025% | 0.035% | 0.040% | 0.040% |
| Polysorbate 80 | — | — | 1.00% | 2.00% | 2.00% |
| Poloxamer 407 | — | — | 1.00% | 0.50% | — |
| Poloxamer 188 | — | — | 0.20% | 0.50% | — |
| HPγCD | — | — | 1.50% | — | — |
| Polyoxyl Castor Oil | — | — | 0.015% | — | — |
| Mannitol | — | — | 1.00% | 0.50% | 0.50% |
| NaCl | 0.09% | 0.09% | 0.40% | 0.40% | 0.40% |
| HPMC or CMC | — | — | 0.50% | 1.20% | 1.20% |
| BAK | 0.01% | 0.01% | 0.01% | 0.01% | 0.01% |
| Boric acid | — | — | 4 mM | 5 mM | 5 mM |
| pH | 6.5 | 7.0 | 7.5 | 7.5 | 7.5 |
| Results | | | | | |
| Weeks of peak miosis | 3 | ≥4 | ≥4 | ≥4 | — |
| Average miosis (during weeks of peak miosis, millimeters) | 1.0 | 1.0 | 1.2 | 1.4 | — |
| Miosis range (millimeters) | 0.5-1.5 | 0.5-1.5 | 0.7-2.0 | 0.8-2.2 | — |
| Duration of peak miosis following instillation (hours) | 4 | 4 | 4.5 | 5 | — |

TABLE 1-continued

Miosis following instillation of brimonidine compositions

| Composition | 1 | 2 | 3 | 4 | 5 |
|---|---|---|---|---|---|
| Whitening (0-4, 4 best) | 2 | 3 | 3.2 | 3.5 | — |
| Hyperemia | Yes | No | No | No | — |

"peak miosis" is the maximum miosis achieved upon instillation of the composition, which for composition 1 is expected to be of limited number of days due to a rebound effect. ">4" denotes peak miosis was achieved for at least 4 weeks and is predicted to not be limited to a particular number of days.

Results

Each subject administered composition 1 experienced only three weeks or less of peak miosis. Further, subjects administered composition 1 experienced eye redness (i.e. hyperemia) due to the relatively high dose of brimonidine. However, subjects administered composition 2 continued to experience peak miosis at the end of the four-week study and none of these subjects experienced hyperemia. Further miosis, whitening and duration of peak miosis following instillation improved when low dose brimonidine was formulated in compositions of the present invention.

EXAMPLE 2 (VIRTUAL)

10 nonpresbyopic (ages 25-39) subject were exposed to a 100-lumen indoor ambient light with their BCDA (corrected distance acuity). On separate days at the same time of day the subjects have their reading speed measured and averaged for each of baseline and after instillation of compositions 1-5 from Table 1, above. Subjects were then asked to rate their eye fatigue after 20 minutes of consecutive reading of written material.

TABLE 2

Eye fatigue, reading speed and pupil size following instillation of a composition of the present invention

| Composition | none | 1 | 2 | 3 | 4 | 5 |
|---|---|---|---|---|---|---|
| Reading speed (wpm) | 50.0 | 50.3 | 50.5 | 50.7 | 50.9 | 51.1 |
| Pupil size (mm) | 3.3 | 3.1 | 2.90 | 2.70 | 2.55 | 2.40 |
| Pupil area (mm$^2$) | 10.89 | 9.61 | 8.41 | 7.29 | 6.50 | 5.29 |
| Pupil size difference vs. baseline (mm$^2$) | — | 1.28 | 2.48 | 3.60 | 4.39 | 5.60 |
| Eye fatigue 0-5) | 2.0 | 1.8 | 1.6 | 1.4 | 1.20 | 1.0 |
| % Relief eye fatigue | — | 10% | 20% | 30% | 40% | 50% |

Following instillation of compositions 1-5, subjects experienced reduction in eye fatigue proportional to the reduction in the size of their pupil (i.e. from 10% to 50%).

What is claimed is:

1. A method of improving night vision comprising administering to an eye of subject in need thereof a composition comprising from about 0.01% to about 0.050% w/v brimonidine, from about 1% to about 5% w/v of a nonionic surfactant and a viscosity enhancer, wherein w/v denotes weight by total volume of the composition and wherein the composition has a pH from about 6.0 to about 8.0.

2. The method of claim 1, wherein brimonidine is at a concentration from about 0.025% to about 0.05% w/v.

3. The method of claim 1, wherein the nonionic surfactant is selected from the group consisting of a polysorbate, a poloxamer, a polyoxyl, an alkyl aryl poly ether, a cyclodextrin, a tocopheryl polyethylene glycol succinate and a combination thereof.

4. The method of claim 3, wherein the nonionic surfactant is a polysorbate.

5. The method of claim 4, wherein the polysorbate is polysorbate 80 and the viscosity enhancer is selected from hydroxypropyl methyl cellulose and carboxymethyl cellulose at a concentration from about 0.1% to about 2% w/v.

6. The method of claim 1, further comprising from about 0.1% to about 5% w/v mannitol.

7. The method of claim 6, wherein the viscosity enhancer is from about 1.0% to about 1.25% w/v hydroxypropyl methyl cellulose.

8. The method of claim 7, wherein the composition further comprises from about 1 to about 10 millimolar boric acid and from about 0.05% to about 0.5% w/v sorbate.

9. The method of claim 1, wherein administration occurs once or twice daily.

10. The method of claim 9, wherein the improvement of night vision occurs for at least four weeks without tachyphylaxis.

11. The method of claim 1, wherein a pupil of the eye of the subject is reduced diameter by 0.5 millimeters or more for 6 or more hours.

12. A method of improving eye fatigue under a luminance level below 500 candela per square meter (cd/m$^2$) comprising administering to an eye of subject in need thereof a composition comprising from about 0.01% to about 0.05% w/v brimonidine, from about 1% to about 5% w/v of a polysorbate and a viscosity enhancer, optionally mannitol 0.10-2.0%, optionally HPMC 0.10%-1.20%, wherein w/v denotes weight by total volume of the composition and wherein the composition has a pH from about 6.0 to about 8.0.

13. The method of claim 12, wherein the luminance levels is below 10 cd/m$^2$.

14. The method of claim 13, wherein the luminance level is below $1 \times 10^{-3}$ cd/m$^2$.

15. A method of improving sports performance under a luminance level below 500 candelas per square meter (cd/m$^2$) comprising administering to an eye of subject in need thereof a composition comprising from about 0.01% to about 0.05% w/v brimonidine, from about 1% to about 5% w/v of a nonionic surfactant and a viscosity enhancer, wherein w/v denotes weight by total volume of the composition and wherein the composition has a pH from about 6.0 to about 8.0.

16. The method of claim 15 wherein the luminance level is below 10 cd/m$^2$.

17. The method of claim 16, wherein the luminance level is below $1 \times 10^{-3}$ cd/m$^2$.

* * * * *